(12) United States Patent
Batzer

(10) Patent No.: US 10,267,839 B2
(45) Date of Patent: Apr. 23, 2019

(54) ELECTRODE-STATUS-DETERMINING FACILITY AND METHOD FOR DETERMINING ELECTRODE STATUS INFORMATION

(71) Applicant: Siemens Healthcare GmbH, Erlangen (DE)

(72) Inventor: Ulrich Batzer, Buckenhof (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 13 days.

(21) Appl. No.: 15/259,274

(22) Filed: Sep. 8, 2016

(65) Prior Publication Data

US 2017/0089970 A1 Mar. 30, 2017

(30) Foreign Application Priority Data

Sep. 24, 2015 (DE) ........................ 10 2015 218 332

(51) Int. Cl.
  *G01R 31/02* (2006.01)
  *A61B 5/0424* (2006.01)
  *G01R 17/02* (2006.01)
  *A61B 5/055* (2006.01)

(52) U.S. Cl.
  CPC .......... *G01R 31/026* (2013.01); *A61B 5/0424* (2013.01); *A61B 5/055* (2013.01); *A61B 2562/0209* (2013.01); *G01R 17/02* (2013.01)

(58) Field of Classification Search
  None
  See application file for complete search history.

(56) References Cited

U.S. PATENT DOCUMENTS 7,519,413 B1 4/2009 Morris
2010/0007413 A1 1/2010 Herleikson
(Continued)

FOREIGN PATENT DOCUMENTS

CN 101534708 A 9/2009
CN 102755161 A 10/2012
(Continued)

OTHER PUBLICATIONS

Venkatesh Acharya: "Improving Common-Mode Rejection Using the Right-Leg Drive Amplifier". Texas Instruments, Application Report. SBAA188, Jul. 2011. http://www.ti.com/lit/an/sbaa188/sbaa188.pdf; 2011.
(Continued)

*Primary Examiner* — Jermele M Hollington
(74) *Attorney, Agent, or Firm* — Harness, Dickey & Pierce, P.L.C.

(57) ABSTRACT

A method is for determining electrode status information relating to an electrode in a differential voltage measuring system for measuring a bioelectric signal, the electrode status information indicating whether the electrode is connected or not connected. An embodiment of the method includes the acquisition of a temporal profile of an electric current flowing through a shunt resistor, wherein the shunt resistor is arranged in series with the electrode in an electric transmission path of the differential voltage measuring system, and the determination of the electrode status information on the basis of the temporal profile.

4 Claims, 6 Drawing Sheets

(56) References Cited

U.S. PATENT DOCUMENTS

| | | | |
|---|---|---|---|
| 2011/0034209 A1* | 2/2011 | Rubinsky | G06F 19/321 |
| | | | 455/556.1 |
| 2012/0095330 A1* | 4/2012 | Shechter | A61B 5/06 |
| | | | 600/424 |
| 2012/0157807 A1 | 6/2012 | Virtanen | |
| 2013/0041421 A1 | 2/2013 | Lu et al. | |
| 2015/0160266 A1 | 6/2015 | Bogner et al. | |
| 2016/0033603 A1* | 2/2016 | Paul | G01R 33/4818 |
| | | | 324/309 |
| 2016/0095528 A1 | 4/2016 | Batzer et al. | |
| 2016/0228024 A1 | 8/2016 | Batzer et al. | |

FOREIGN PATENT DOCUMENTS

| | | |
|---|---|---|
| CN | 203634155 U | 6/2014 |
| DE | 10353970 A1 | 7/2005 |
| DE | 102014018182 A1 | 6/2015 |
| DE | 102015202447 A1 | 8/2016 |
| DE | 102014219943 A1 | 4/2018 |
| EP | 2443995 A3 | 2/2013 |
| WO | WO 2014138356 A1 | 9/2014 |

OTHER PUBLICATIONS

Anthony Calabria: "Understanding Lead-Off Detection in ECG". Texas Instruments, Application Report. SBAA196A, May 2012, Revised Jan. 2015. http://www.ti.com/lit/an/sbaa196a/sbaa196a.pdf.

German Office Action dated Jun. 3, 2016.

Office Action for Chinese Patent Application No. 201610851699.1 dated Jan. 17, 2019 and English translation thereof.

* cited by examiner

ELECTRODE-STATUS-DETERMINING FACILITY AND METHOD FOR DETERMINING ELECTRODE STATUS INFORMATION

PRIORITY STATEMENT

The present application hereby claims priority under 35 U.S.C. § 119 to German patent application number DE 102015218332.7 filed Sep. 24, 2015, the entire contents of which are hereby incorporated herein by reference.

FIELD

At least one embodiment of the invention generally relates to a method for determining electrode status information relating to an electrode of a differential voltage measuring system for measuring a bioelectric signal, wherein the electrode status information indicates whether the electrode is connected or not connected. At least one embodiment of the invention further generally relates to an electrode-status-determining facility, a differential voltage measuring system, an arrangement comprising an imaging device and a differential voltage measuring system, a computer program product and a computer-readable medium.

BACKGROUND

With applications entailing the measurement of a bioelectric signal, for example an electrocardiogram signal (ECG signal), via a differential voltage measuring system, it is advantageous to be able to identify whether an electrode of the differential voltage measuring system is connected or not connected to a patient. This in particular relates to applications in which a further action, for example the controlling and/or triggering of an imaging device on the basis of the bioelectric signal, is carried out. If an electrode is identified as being connected even though it is not connected, triggers could be initiated erroneously. If an electrode is identified as not connected even though it is connected, valid triggers could be suppressed. Therefore there is a requirement for electrode status information that indicates whether the electrode is connected or not connected to be determined as quickly and accurately as possible. Hereinafter, an electrode status of an electrode should be understood to mean electrode status information relating to the electrode, wherein the electrode status information indicates whether the electrode is connected or not connected.

The electrode status of an electrode of an ECG system for measuring an ECG signal can, for example, be determined in that the signal quality of the ECG signal is analyzed and, on the basis thereof, conclusions drawn regarding the electrode status. Since an ECG signal can also have multifarious forms when the electrodes of the ECG system are correctly connected to the patient, such an analysis of the signal quality of the ECG signal has to be very tolerant. This means that in many cases it is not possible to identify an open connection quickly, i.e. in fewer than 100 milliseconds, but that a deficient signal quality indicative of an open connection is only identified after an analysis lasting several seconds.

A return-path method for determining the electrode status of a first electrode is, for example, known from [AC12]. In this context, a test current in the nanoampere range is impressed on the first electrode via a current source. If the first electrode is connected, the test current flows through the patient and a corresponding return path connected to the patient via at least one further electrode. The return path can, for example, comprise a measuring path of the differential voltage measuring system and/or a transmission path right-leg drive facility of the differential voltage measuring system. In this case, the voltage effected by the current source at the first electrode is at the most in the millivolt range since the test current in the nanoampere range flows through an impedance, which is at the most in the megohm range. If the first electrode and/or the return path is not connected, the electric circuit is not closed or the impedance to be overcome by the test current is much greater so that the voltage effected by the current source at the first electrode goes to saturation, which can, for example, be identified by a comparator. Due to the required return path, this only enables the electrode status of the first electrode to be determined if at least one further electrode is connected to the patient.

Patent application No 10 2015 202 447.4 describes a differential voltage measuring system with a right-leg drive facility. [VA11] discloses an ECG system with a right-leg drive facility. The person skilled in the art is in particular familiar with is a right-leg drive facility in particular under the term "right-leg drive", which is abbreviated to "RLD". In this context, the reference to the right leg is solely based on conventional use. The side of the patient or extremity of the patient to which the right-leg drive circuit, in particular the RLD electrode, is connected is immaterial for the technical effect of the right-leg drive circuit. In the case of a non-conventional connection of the RLD electrode to the patient, it might be necessary to adapt measuring electrodes of the differential voltage measuring system appropriately in each case with respect to the position relative to the RLD electrode.

SUMMARY

At least one embodiment of the invention enables improved determination of electrode status information.

At least one embodiment is directed to a method, an electrode-status-determining facility, a differential voltage measuring system, an arrangement, a computer program product and/or a computer-readable medium.

The method according to at least one embodiment of the invention for determining electrode status information, which relates to an electrode of a differential voltage measuring system for measuring a bioelectric signal, wherein the electrode status information indicates whether the electrode is connected or not connected, acquires a temporal profile of an electric current flowing through a shunt resistor, wherein the shunt resistor is arranged in series with the electrode in an electric transmission path of the differential voltage measuring system and determines the electrode status information on the basis of the temporal profile.

The electrode-status-determining facility according to at least one embodiment of the invention for determining electrode status information relating to an electrode of a differential voltage measuring system for measuring a bioelectric signal, wherein the electrode status information indicates whether the electrode is connected or not connected, comprises an acquisition module and a determination module. The acquisition module is embodied for the acquisition of a temporal profile of an electric current flowing through a shunt resistor, wherein the shunt resistor is arranged in series with the electrode in an electric transmission path of the differential voltage measuring system. The determination module is embodied for the determination of electrode status information on the basis of the profile. According to one embodiment of the invention, the electrode-status-determining facility is embodied to carry out a method according to at least one embodiment of the invention for determining electrode status information.

The electrode-status-determining facility according to at least one embodiment of the invention for determining electrode status information relating to an electrode of a differential voltage measuring system for measuring a bioelectric signal, the electrode status information indicating whether the electrode is connected or not connected, the electrode-status-determining facility comprising:

a memory storing computer-readable instructions; and
one or more processors configured to execute the computer-readable instructions such that the one or more processors are configured to
acquire a temporal profile of an electric current flowing through a shunt resistor, the shunt resistor being arranged in series with the electrode in an electric transmission path of the differential voltage measuring system, and
determine the electrode status information on the basis of the acquired temporal profile.

The computer program product according to at least one embodiment of the invention comprises a computer program, wherein the computer program can be loaded into a memory facility of a computer, wherein the computer program carries out the steps of a method according to at least one embodiment of the invention for determining electrode status information when the computer program is executed on the computer. In addition to the computer program, the computer program product comprises additional software components, for example documentation, and/or hardware components, for example a hardware key (dongle etc.) for using the software.

A memory including a computer program stored therein, wherein the computer program is loadable into a memory facility of a computer, the computer program being configured to execute the method of according to at least one embodiment of the invention for determining electrode status information when the computer program is executed on the computer. In addition to the computer program, the memory may include additional software components, for example documentation, and/or hardware components, for example a hardware key (dongle etc.) for using the software.

A computer program of at least one embodiment is stored on the computer-readable medium, wherein the computer program can be loaded into a memory facility of a computer, wherein the computer program carries out the steps of a method according to at least one embodiment of the invention for determining electrode status information when the computer program is executed on the computer. The computer-readable medium can, for example, be a memory stick, a hard disk or another transportable or permanently installed data medium. The computer-readable medium can be embodied to transport the computer program to the control device and/or to store the computer program on or in the control device.

At least one embodiment of the invention further relates to a method for determining electrode status information relating to an electrode of a differential voltage measuring system for measuring a bioelectric signal, wherein the electrode status information indicates whether the electrode is connected or not connected, wherein the method comprises the following steps:

the acquisition of a temporal profile of an electric voltage dropping at a shunt resistor via a voltage measuring facility, which is switched parallel to the shunt resistor, wherein the shunt resistor is arranged in series with the electrode in an electric transmission path of the differential voltage measuring system, the determination of the electrode status information on the basis of the temporal profile.

The arrangement according to at least one embodiment of the invention comprises an imaging device and a differential voltage measuring system according to at least one embodiment of the invention. According to one embodiment of the invention, the imaging device comprises a control device, a raw imaging data acquisition device and an image reconstruction facility, wherein the control device is embodied to control the raw imaging data acquisition device and/or the image reconstruction facility on the basis of the bioelectric signal. The control device can, for example, be a computer. In particular, the electrode-status-determining facility according to at least one embodiment of the invention can be embodied as part of the control device of the imaging device. One embodiment of the invention provides that the control device comprises a processor system. The processor system can, for example, be formed by one or more interacting microprocessors.

BRIEF DESCRIPTION OF THE DRAWINGS

The invention is described again in more detail below with reference to the attached figures and with reference to example embodiments. The depiction in the figures is schematic, greatly simplified and not necessarily true to scale.

The figures show.

DETAILED DESCRIPTION OF THE EXAMPLE EMBODIMENTS

Figure 1:
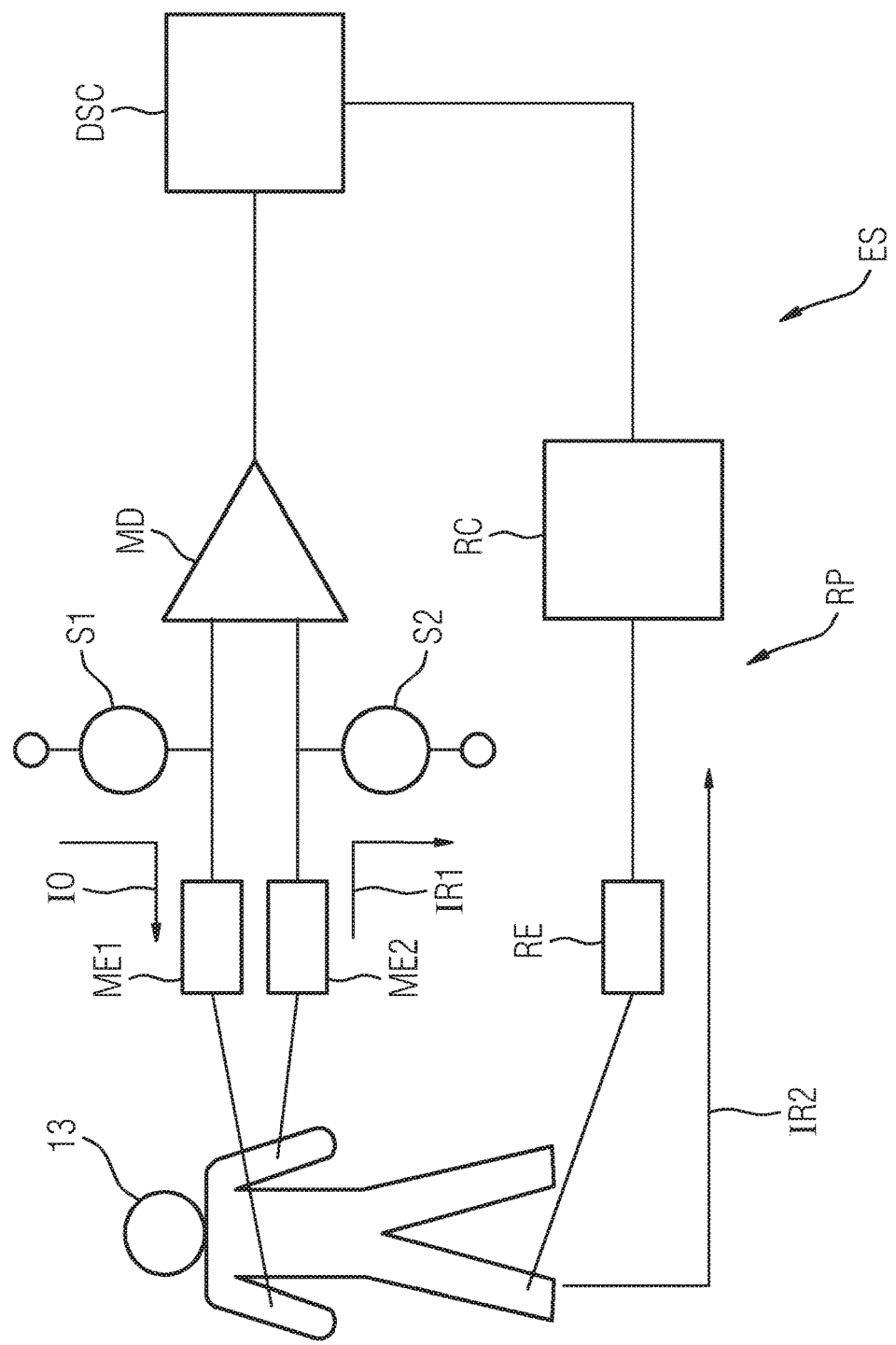
FIG. 1 an ECG system embodied for electrode status identification according to the return-path method, FIG. 2 a flowchart of a method according to a first embodiment of the invention, FIG. 3 a depiction of an electrode-status-determining facility according to a second embodiment of the invention, FIG. 4 a differential voltage measuring system according to a third embodiment of the invention, FIG. 5 a depiction of the temporal profile of the electric current flowing through the shunt resistor according to the third embodiment of the invention, FIG. 6 a depiction of a bioelectric signal measured with the differential voltage measuring system according to the third embodiment of the invention, FIG. 7 an arrangement according to a fourth embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention for determining electrode status information, which relates to an electrode of a differential voltage measuring system for measuring a bioelectric signal, wherein the electrode status information indicates whether the electrode is connected or not connected, acquires a temporal profile of an electric current flowing through a shunt resistor, wherein the shunt resistor is arranged in series with the electrode in an electric transmission path of the differential voltage measuring system and determines the electrode status information on the basis of the temporal profile.

The inventor suggests the determination of the electrode status information with aid of a shunt resistor arranged in series with the electrode in an electric transmission path of the differential voltage measuring system. The inventor has recognized that a temporal profile of an electric current flowing through the shunt resistor is significantly dependent upon whether the electrode is connected or not connected to the patient.

The inventor has in particular recognized that, when the patient is located in an stray electromagnetic field, a current can flow through the shunt resistor, which, when the electrode is connected to the patient, is significantly greater, for example by one or more orders of magnitude, than when the electrode is not connected to the patient. The stray electromagnetic field can, for example, be generated by one or more electrical apparatuses and/or one or more electric supply lines.

One embodiment of the invention provides that the bioelectric signal is a bioelectric signal of the patient and/or that the electrode status information indicates whether the electrode is connected to the patient or is not connected to the patient. One embodiment of the invention provides that the differential voltage measuring system is an electrocardiogram system (ECG system) and/or that the bioelectric signal is an electrocardiogram signal (ECG signal).

According to one embodiment of the invention, the differential voltage measuring system comprises a right-leg drive facility, wherein the right-leg drive facility comprises the electrode and the transmission path.

Hereinafter, an RLD electrode in particular means the electrode of the right-leg drive facility of the differential voltage measuring system. Hereinafter, a measuring electrode in particular means an electrode of a differential input stage of the differential voltage measuring system. One embodiment of the invention provides that the electrode status information relates to a measuring electrode of the differential voltage measuring system, wherein the electrode status information indicates whether the measuring electrode is connected or not connected.

In many cases, the electrode status of the RLD electrode cannot be determined directly using the return-path method since the RLD electrode is regulated in order to suppress a common-mode interference signal on a right-leg drive-signal which can conflict with a current which is additionally impressed in order to determine the electrode status.

The electrode status of the RLD electrode can be determined indirectly using the return-path method in that, for a plurality of electrodes, the return path is in each case selected via the RLD electrode. If the RLD electrode is not connected, an open connection is identified simultaneously for the plurality of measuring electrodes. However, the same result is obtained if the plurality of measuring electrodes is actually not connected and it is hence not unequivocal. Since the return path for each of the plurality of measuring electrodes can in each case be selected via another measuring electrode, it is possible for an electrode status to be determined for each of the plurality of measuring electrodes even if the RLD electrode is not connected to the patient. Hence, the return-path method is only suitable for the determination of electrode status information relating to the RLD electrode with certain restrictions.

Since the right-leg drive facility can be important with respect to the suppression of a common-mode interference signal, it is advantageous to be able to measure the electrode status of the RLD electrode as directly as possible. In the case of relatively minor interference to the bioelectric signal, in some circumstances it can be difficult to determine the electrode status of the RLD electrode from the bioelectric signal. If the interference is relatively strong, the impairment of the bioelectric signal can be much greater in the case of an unconnected RLD electrode than in the case of a connected RLD electrode.

One embodiment of the invention provides that the temporal profile of the electric current flowing through the shunt resistor, which is arranged in series with the RLD electrode, is to a large extent independent of the connection status of the measuring electrodes. Alternatively or additionally to the determination of the electrode status, the temporal profile can be used to suppress a common-mode interference signal, such as, for example, described in German patent application No 10 2015 202 447.4, the entire contents of which are hereby incorporated herein by reference.

According to one embodiment of the invention, a deviation of the temporal profile from a reference profile is determined, wherein the electrode status information is determined on the basis of the deviation. One embodiment of the invention provides that the reference profile is a constant profile. For example, the constant profile can have the same value at all times, for example the value zero.

According to one embodiment of the invention, the electrode status information is determined on the basis of a threshold condition for the temporal profile. One embodiment of the invention provides that the electrode status information is determined on the basis of a threshold condition for the deviation. One embodiment of the invention provides that the threshold condition is only considered to be satisfied when the electrode is connected or that the threshold condition is only considered to be satisfied when the electrode is not connected.

The threshold condition can, for example, relate to a parameter of the temporal profile and/or a parameter of the deviation, wherein the parameter is selected from the group consisting of an amplitude, a voltage, a current, an energy and a power. The parameter can in particular be averaged with respect to a time interval.

One embodiment of the invention provides that the threshold condition is only satisfied when the parameter and/or the deviation exceeds a specified threshold value or that the threshold condition is only satisfied when the parameter and/or the deviation falls below a specified threshold value.

According to one embodiment of the invention, a component of the temporal profile is determined in a specified frequency range, wherein the electrode status information is determined on the basis of the component. The component can, for example, be determined by filtering. The parameter can in particular be determined on the basis of the component.

According to one embodiment of the invention, the specified frequency range is defined by a frequency of a stray electromagnetic field. The stray field can in particular be an alternating field. In particular, the frequency of the alternating field can be the mains frequency of an electric power supply network. The stray field can, for example, be generated by one or more electric apparatuses and/or one or more electric lines. In particular, the electric apparatus or electric apparatuses and/or the electric line or electric lines can be located in the vicinity of the patient and/or connected to the power supply network.

One embodiment of the invention provides that the patient is located in the stray field. Hence, the patient can function as a receiving antenna for the stray field so that a higher current flows through the shunt resistor when the electrode is connected to the patient. Hence, the electrode status information can be determined on the basis of a threshold condition, which is only satisfied when a parameter, for example an amplitude or a power, of the temporal profile of the current exceeds a specified threshold value. Hence, the invention in particular enables the direct determination of the electrode status of the RLD electrode independently of the measuring electrodes.

The electrode-status-determining facility according to at least one embodiment of the invention for determining electrode status information relating to an electrode of a differential voltage measuring system for measuring a bioelectric signal, wherein the electrode status information indicates whether the electrode is connected or not connected, comprises an acquisition module and a determination module. The acquisition module is embodied for the acquisition of a temporal profile of an electric current flowing through a shunt resistor, wherein the shunt resistor is arranged in series with the electrode in an electric transmission path of the differential voltage measuring system. The determination module is embodied for the determination of electrode status information on the basis of the profile. According to one embodiment of the invention, the electrode-status-determining facility is embodied to carry out a method according to at least one embodiment of the invention for determining electrode status information.

The differential voltage measuring system according to at least one embodiment of the invention for measuring a bioelectric signal comprises an electrode, a shunt resistor arranged in series with the electrode in an electric transmission path of the differential voltage measuring system and an electrode-status-determining facility according to at least one embodiment of the invention.

According to one embodiment of the invention, the differential voltage measuring system comprises a right-leg drive facility, wherein the right-leg drive facility comprises the electrode and the transmission path.

According to one embodiment of the invention, the differential voltage measuring system comprises a voltage measuring facility, which is switched parallel to the shunt resistor, wherein the voltage measuring facility can be used to measure the electric voltage dropping across the shunt resistor and hence the current flowing through the shunt resistor.

At least one embodiment of the invention further relates to a method for determining electrode status information relating to an electrode of a differential voltage measuring system for measuring a bioelectric signal, wherein the electrode status information indicates whether the electrode is connected or not connected, wherein the method comprises the following steps:

the acquisition of a temporal profile of an electric voltage dropping at a shunt resistor via a voltage measuring facility, which is switched parallel to the shunt resistor, wherein the shunt resistor is arranged in series with the electrode in an electric transmission path of the differential voltage measuring system, the determination of the electrode status information on the basis of the temporal profile.

The arrangement according to at least one embodiment of the invention comprises an imaging device and a differential voltage measuring system according to at least one embodiment of the invention. According to one embodiment of the invention, the imaging device comprises a control device, a raw imaging data acquisition device and an image reconstruction facility, wherein the control device is embodied to control the raw imaging data acquisition device and/or the image reconstruction facility on the basis of the bioelectric signal. The control device can, for example, be a computer. In particular, the electrode-status-determining facility according to at least one embodiment of the invention can be embodied as part of the control device of the imaging device. One embodiment of the invention provides that the control device comprises a processor system. The processor system can, for example, be formed by one or more interacting microprocessors.

One embodiment of the invention provides that the temporal profile of the electric current is acquired in that measurement data relating to the electric current is received. A further embodiment of the invention provides that the temporal profile of the electric current is acquired in that measurement data relating to the electric current is measured and received. The measurement data can, for example, be measured via a voltage measuring facility, which is switched in parallel to the shunt resistor. The measurement data can, for example, be received via the acquisition module. In particular, the acquisition module can comprise a measurement-data-receiving unit embodied to receive the measurement data, and/or the voltage measuring facility.

According to one embodiment of the invention, the imaging device is selected from the imaging-modality group consists of an X-ray apparatus, a computed tomography apparatus (CT apparatus), a C-arm-X-ray apparatus, a single-photon-emission computed tomography apparatus (SPECT apparatus), a positron emission tomography apparatus (PET apparatus), a magnetic resonance tomography apparatus, an ultrasound apparatus and combinations thereof. The imaging device can in particular be a combination of one or more imaging modalities selected in each case from the imaging-modality group, and/or one or more irradiation modalities, for example a PET-CT apparatus or a SPECT-CT apparatus. In this context, an irradiation modality can, for example, comprise an irradiation device for therapeutic irradiation.

The computer program product according to at least one embodiment of the invention comprises a computer program, wherein the computer program can be loaded into a memory facility of a computer, wherein the computer program carries out the steps of a method according to at least one embodiment of the invention for determining electrode status information when the computer program is executed on the computer. In addition to the computer program, the computer program product comprises additional software components, for example documentation, and/or hardware components, for example a hardware key (dongle etc.) for using the software.

A computer program of at least one embodiment is stored on the computer-readable medium, wherein the computer program can be loaded into a memory facility of a computer, wherein the computer program carries out the steps of a method according to at least one embodiment of the invention for determining electrode status information when the computer program is executed on the computer. The computer-readable medium can, for example, be a memory stick, a hard disk or another transportable or permanently installed data medium. The computer-readable medium can be embodied to transport the computer program to the control device and/or to store the computer program on or in the control device.

Within the scope of the invention, it is possible to combine features, which are described with respect to different embodiments and/or different claim categories to form further embodiments. In other words, the substantive claims can also be developed with the features described or claimed in connection with a method. In this context, functional features of the method can be formed by correspondingly embodied modules.

The use of the indefinite article "a" or "an" does not preclude the possibility of the elements in question also being present on a multiple basis. The use of a given ordinal number in connection with a given element serves to provide better differentiation of the given element from other elements and does not mean that in each case an element has to be present for all the ordinal numbers preceding the given ordinal number. For example, the arrangement according to at least one embodiment of the invention can comprise a third element, for example the third layer, without a second element, for example the second layer, being present.

The invention is not restricted by the disclosed embodiments and examples. Further variations can be derived by the person skilled in the art without departing from the scope of the invention as defined by the claims.

FIG. 1 shows an ECG system ES embodied to identify an electrode status according to the return-path method. The ECG system ES comprises a differential input stage MD with a first measuring electrode ME1 and a second measuring electrode ME2 and a right-leg drive facility RP with a drive circuit RC and a RLD electrode RE. The first electrode ME1 is impressed with a test current I0 in the nanoampere range via the first current source S1 and/or the second current source S2. FIG. 1 depicts a possible first return path IR1 through the patient 13 and the second measuring electrode ME2 and a possible second return path IR2 through the patient 13 and the RLD electrode RE. With respect to further details of the return-path method, reference is made to [AC12].

Figure 2:
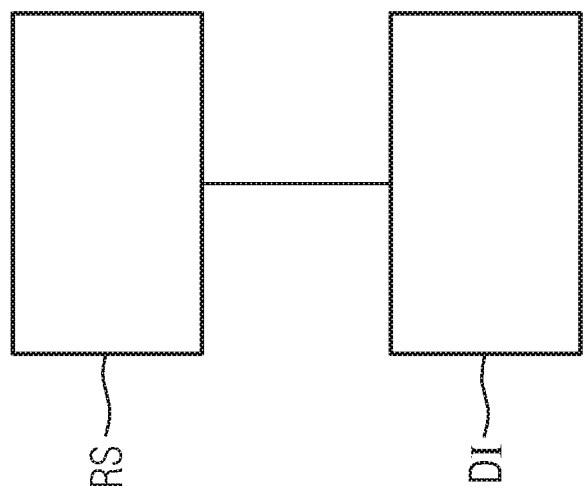

FIG. 2 is a flowchart of a method for determining electrode status information relating to a connection status of an electrode RE of a differential voltage measuring system DS for measuring a bioelectric signal BS according to a first embodiment of the invention. In Step RS, a temporal profile of an electric current RI flowing through a shunt resistor RR is acquired, wherein the shunt resistor RR is arranged in series with the electrode RE in an electric transmission path RT of the differential voltage measuring system DS.

In Step RS, it is, for example, possible to acquire a temporal profile of an electric voltage RV dropping across the shunt resistor RR via the voltage measuring facility RD, which is switched parallel to the shunt resistor RR. This enables the electric current RI flowing through the shunt resistor RR to be measured via the voltage measuring facility RD.

In Step DI, the electrode status information is determined on the basis of the temporal profile.

Figure 3:
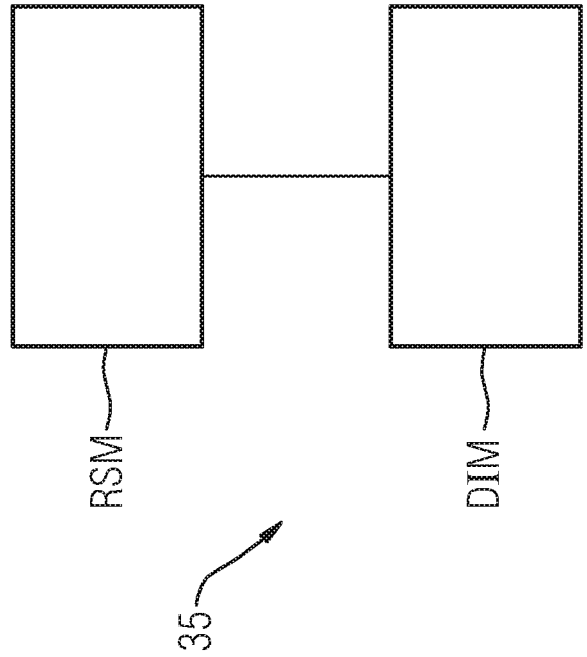

FIG. 3 shows a depiction of an electrode-status-determining facility 35 according to a second embodiment of the invention. The electrode-status-determining facility 35 is embodied for the determination of electrode status information relating to a connection status of an electrode RE of a differential voltage measuring system DS for measuring a bioelectric signal BS and comprises an acquisition module RSM and a determination module DIM. The acquisition module RSM is embodied for the acquisition RS of a temporal profile of an electric current RI flowing through a shunt resistor RR, wherein the shunt resistor RR is arranged in series with the electrode RE in an electric transmission path RT of the differential voltage measuring system DS. The determination module DIM is embodied for the determination DI of the electrode status information on the basis of the profile. The electrode-status-determining facility 35 is embodied to carry out a method according to the first embodiment of the invention.

Figure 4:
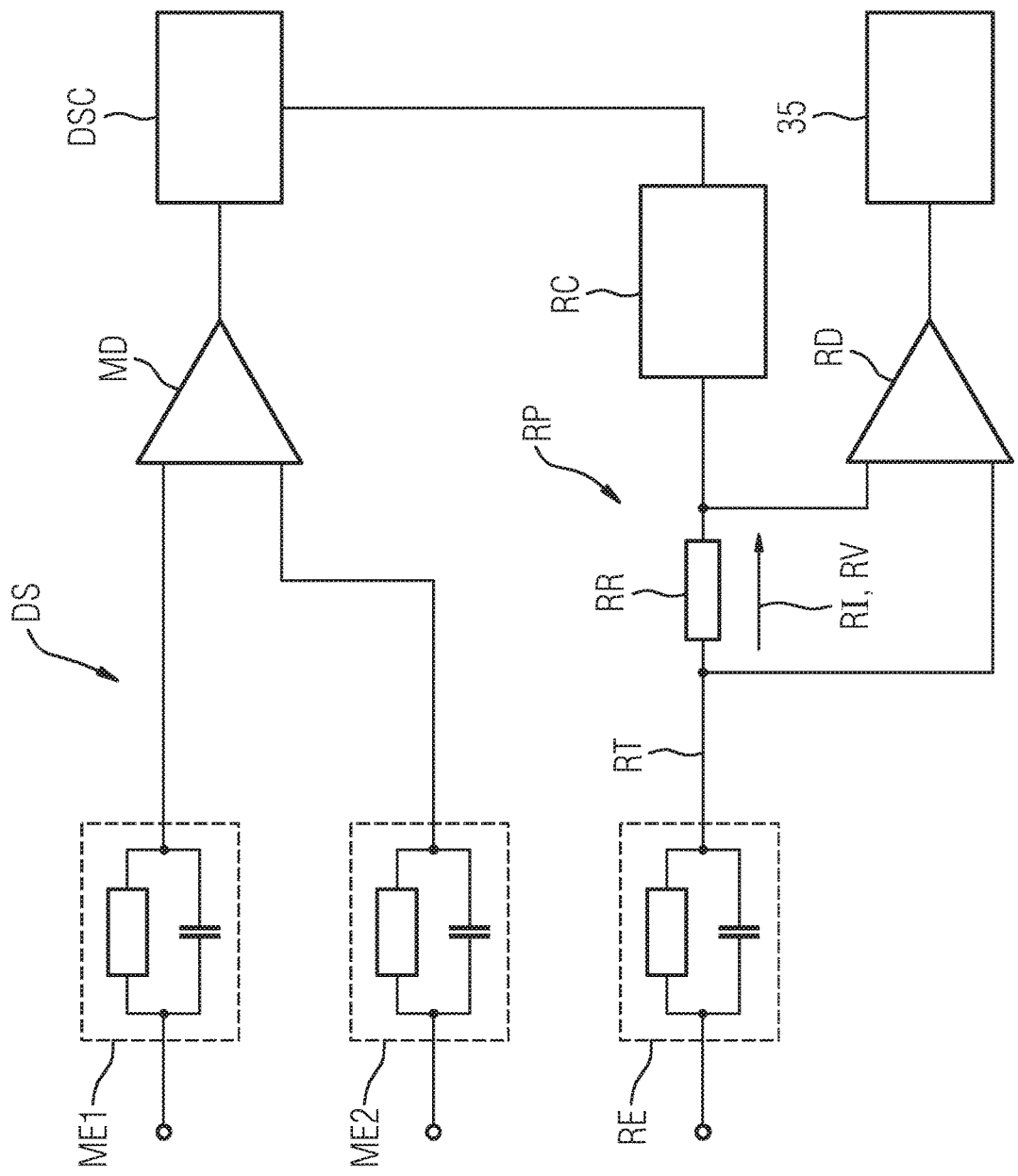

FIG. 4 shows a differential voltage measuring system DS for measuring a bioelectric signal BS according to a third embodiment of the invention. According to the third embodiment of the invention, the differential voltage measuring system DS is an ECG system. The differential voltage measuring system DS comprises an electrode RE, a shunt resistor RR connected in series with the electrode RE in an electric transmission path RT of the differential voltage measuring system DS and the electrode-status-determining facility 35 according to the second embodiment of the invention. The differential voltage measuring system DS comprises a right-leg drive facility RP, wherein the right-leg drive facility RP comprises the electrode RE and the transmission path RT. The differential voltage measuring system DS comprises a voltage measuring facility RD, which is switched in parallel to the shunt resistor RR with which the electric voltage RV dropping across the shunt resistor RR and hence the current RI flowing through the shunt resistor RR can be measured. The differential voltage measuring system DS comprises a voltage measuring system control facility DSC embodied to control the differential voltage measuring system DS. The differential voltage measuring system DS is optionally embodied to suppress a common-mode interference signal on the basis of the temporal profile of the current RI or the voltage RV, such as that described, for example, in German patent application No 10 2015 202 447.4, the entire contents of which are hereby incorporated herein by reference.

The right-leg drive facility RP comprises the drive circuit RC. The shunt resistor RR is arranged in series between the electrode RE and the drive circuit RC of the right-leg drive facility RP.

The differential voltage measuring system DS comprises the differential input stage MD. Alternatively or additionally to the shunt resistor RR depicted in FIG. 4, it is possible for a shunt resistor arranged in series between the electrode ME1 and the differential input stage MD and/or a shunt resistor arranged in series between the electrode ME2 and the differential input stage MD to be provided.

Figure 5:
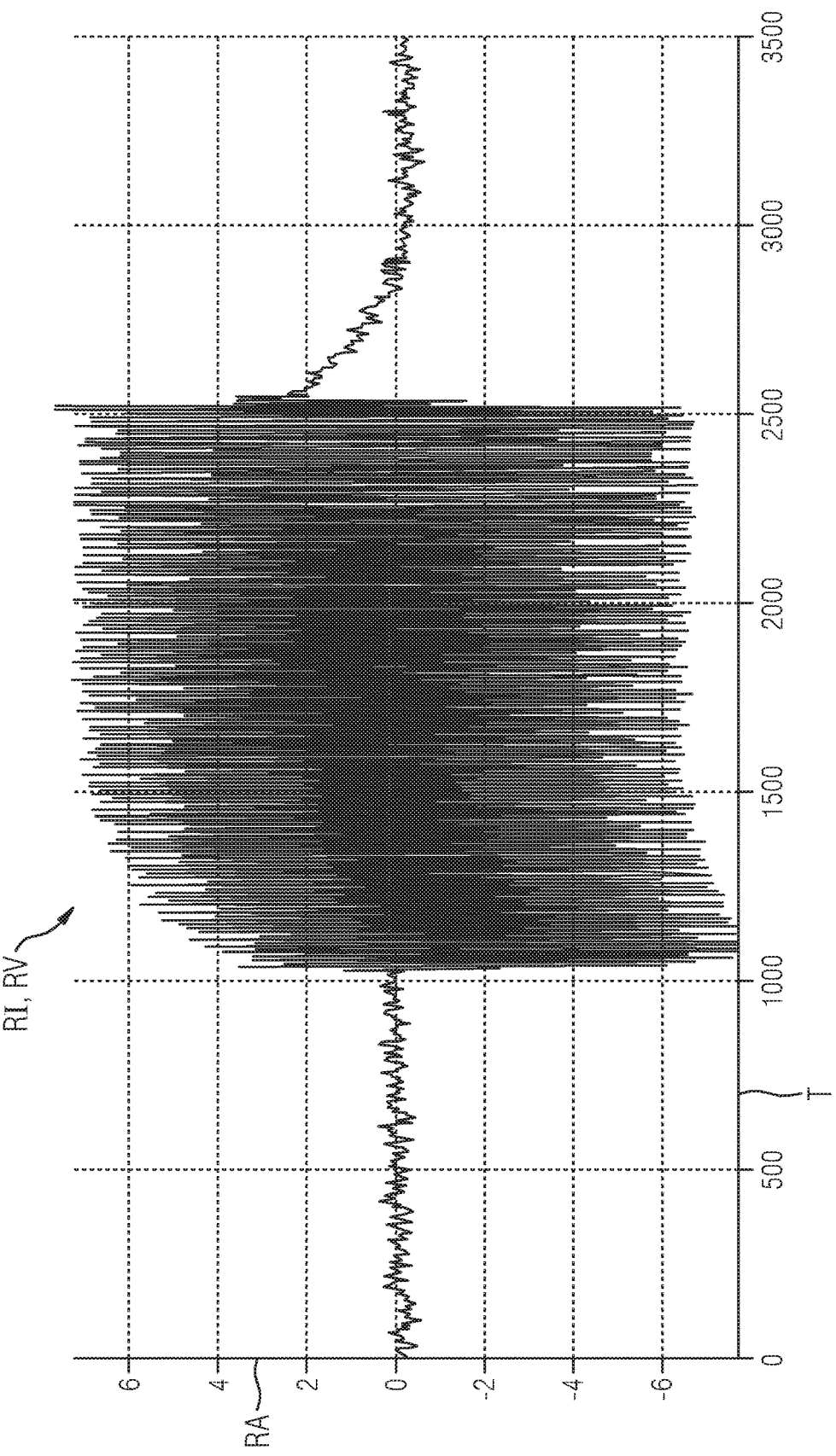

FIG. 5 is a depiction of the temporal profile of the electric current RI flowing through the shunt resistor RR, wherein the shunt resistor RR is arranged in series with the electrode RE in the electric transmission path RT of the differential voltage measuring system DS according to the third embodiment of the invention.

A given time point is depicted on the time axis T, in each case by a given number of temporally equidistant sampling points, also called samples. A value of the electric voltage RV dropping across the shunt resistor RR in millivolts is depicted on the amplitude axis RA. The temporal profile of the current RI corresponds to the temporal profile of the voltage RV. The third embodiment of the invention provides that the value of the shunt resistor RR is equal to 22 kiloohm. The voltage RV can be calculated by multiplying the current RI with the value of the shunt resistor RR, RV=RR·RI.

In the time interval from sample 0 to sample approximately 1000, the RLD electrode RE is not connected to the patient 13. In the time interval from sample approximately 1000 to sample approximately 2500, the RLD electrode RE is connected to the patient 13. In the time interval after sample approximately 2500, the RLD electrode RE is not connected. The amplitude of the temporal profile or a power determined on the basis of the temporal profile is much higher when the RLD electrode RE is connected. In this context, the patient 13 functions as a receiving antenna for a stray electromagnetic field generated by electric apparatuses and/or lines in the environment of the patient. Hence, the temporal profile can be used to determine the electrode status information indicating whether the RLD electrode RE is connected or not connected. The relatively high amplitude or energy when the RLD electrode RE is connected is substantially caused by the component of the temporal profile in the frequency range of the mains frequency. According to the third embodiment of the invention, the mains frequency is equal to 50 hertz.

Figure 6:
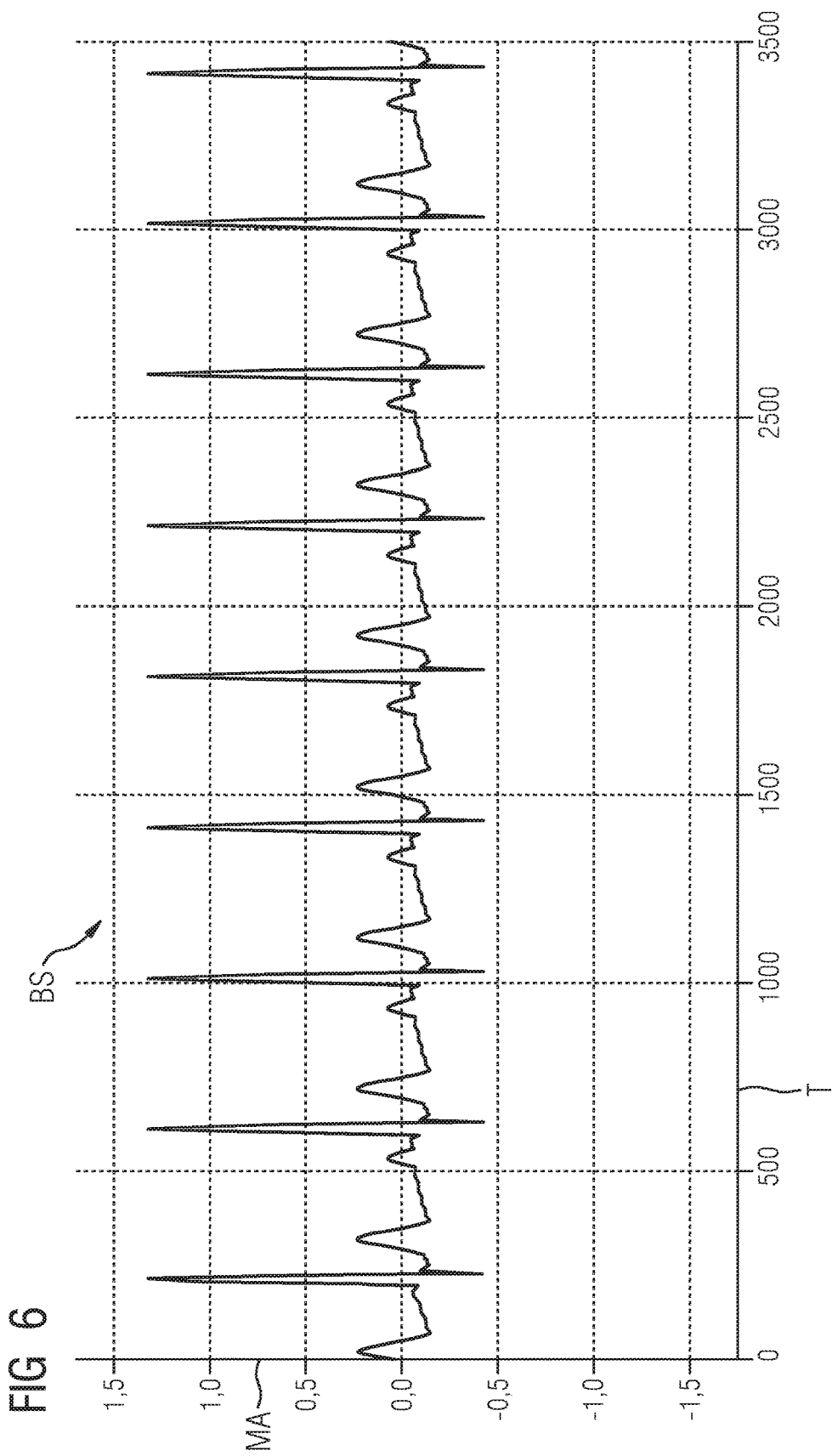

FIG. 6 is a depiction of the bioelectric signal BS which was measured with the differential voltage measuring system DS simultaneously with the current RI of which the temporal profile is depicted in FIG. 5. A value of the bioelectric signal BS in millivolts is depicted on the amplitude axis MA. It is not possible or hardly possible to identify from the temporal profile of the bioelectric signal BS whether the RLD electrode RE is connected or not. Therefore, as long as there is no severe interference, the bioelectric signal BS can optionally also be measured when the RLD electrode RE is not connected.

Hence, the invention enables improved identification of the electrode status, for example within the context of a clinical application and hence a reduction of the time and cost involved. A further advantage of the invention consists in the fact that the electrode status of the RLD electrode RE can be determined independently of the connection status of the measuring electrodes ME1, ME2. In particular, the method according to the invention for determining electrode status information relating to the connection status of an RLD electrode RE and the return-path method to identify the electrode status of one or more electrodes ME1, ME2, can be carried out simultaneously.

If the measuring electrodes ME1, ME2 are not connected, it is often not advisable to continue an examination. If an RLD electrode RE is not connected, it is possible to continue the examination, although there will be more susceptibility to interference. Since the RLD electrode RE makes an important contribution to the suppression of strong interference, but, in some circumstances, is less relevant when there is little interference, it can be advisable in certain situations to continue the examination, even if has been identified that the RLD electrode RE is not connected. This in particular relates to scenarios in which it is no longer necessary to correct the RLD electrode from a certain critical point without interrupting the examination. In such cases, it can be advisable to continue the examination, in particular the measurement of the bioelectric signal BS, despite the increased susceptibility to interference. Typical critical time points from which the termination of the examination is no longer advisable can, in some circumstances for example, be a starting time point, a contrast medium injection and/or a starting time point for the acquisition of raw imaging data via an imaging device 2, in particular using ionizing radiation 27.

Figure 7:
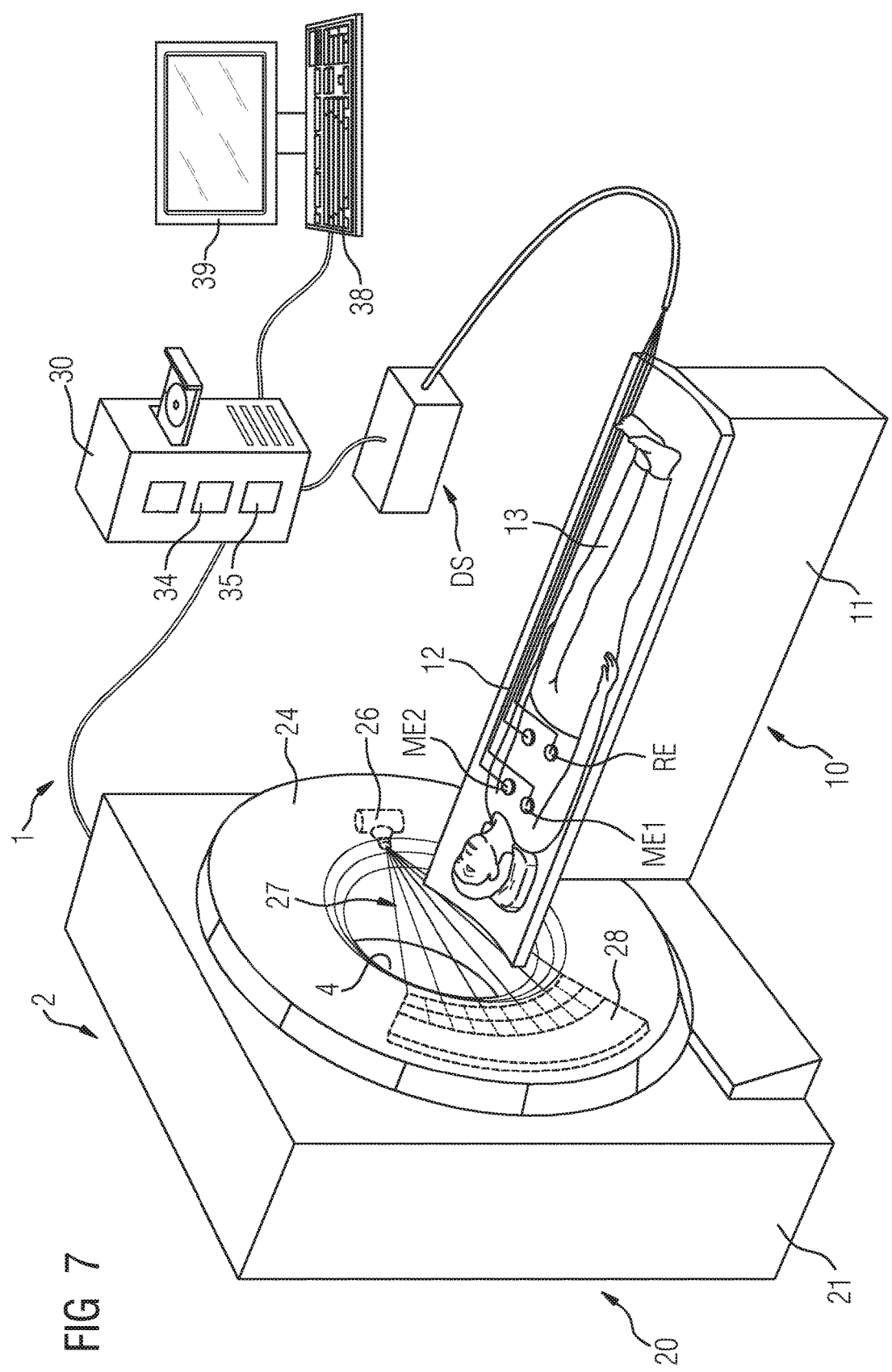

FIG. 7 shows an arrangement 1 according to a fourth embodiment of the invention, wherein the arrangement 1 comprises an imaging device 2 with an acquisition region 4 formed by a tunnel-shaped opening, wherein the patient support device 10 comprises a support table 11, wherein the support plate 12 is arranged movably relative to the support table 11 so that the support plate 12 can be introduced into in the acquisition region 4 in the longitudinal direction of the support plate 12. Without restricting the general concept of the invention, the imaging device 2 shown is, by way of example, a computed tomography apparatus 1.

The imaging device 2 comprises a gantry 20, the acquisition region 4, the patient support device 10, a raw imaging data acquisition device 26, 28 and a control device 30. The gantry 20 comprises a stationary support frame 21 and a rotor 24. The rotor 24 is mounted rotatably about an axis of rotation via a rotary support device. The acquisition region 4 is formed by a tunnel-shaped opening in the gantry 20. A region to be depicted of an object, in particular the patient 13, can be arranged in the acquisition region 4.

According to the fourth embodiment of the invention, the raw imaging data acquisition device 26, 28 is a projection-data-acquisition device 26, 28 with a radiation source 26, for example an X-ray source, and a detector 28, for example an X-ray detector. The radiation source 26 is arranged on the rotor 24 and embodied for the emission of radiation, for example X-rays, with radiation quanta 27. The detector 28 is arranged on the rotor 24 and embodied for the detection of the radiation quanta 27. The radiation quanta 27 can travel from the radiation source 26 to the region to be depicted and, following interaction with the region to be depicted, arrive at the detector 28. This enables projection data of the region to be depicted to be acquired. The projection data acquired by the projection-data-acquisition device 26, 28 is forwarded to the control device 30. The control device 30 is a computer, in particular a digital computer, and embodied to control the imaging device 2. The control device 30 comprises an image reconstruction facility 34 and the electrode-status-determining facility 35 according to the second embodiment of the invention. The image reconstruction facility 34 can be used to reconstruct an image from the projection data.

The imaging device 2 comprises an input device 38 and an output device 39. The input device 38 is embodied for inputting control information, for example image reconstruction parameters and/or examination parameters. The output device 39 is embodied for outputting control information and/or images.

The arrangement 1 according to the fourth embodiment of the invention comprises the differential voltage measuring system DS according to the third embodiment of the invention. The fourth embodiment of the invention provides that the bioelectric signal BS is measured via the differential voltage system DS. The control device 30 can be used to further process the bioelectric signal BS. In particular the bioelectric signal BS can be used to control the imaging device 2, the projection-data-acquisition device 26, 28 and/or the image reconstruction facility 34. For example, the bioelectric signal BS can trigger an acquisition of projection data and/or a selection of projection data for a reconstruction of an image.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

BIBLIOGRAPHY

[VA11]
Venkatesh Acharya: "Improving Common-Mode Rejection Using the Right-Leg Drive Amplifier". Texas Instruments, Application Report. SBAA188, July 2011. http://www.ti.com/lit/an/sbaa188/sbaa188.pdf

[AC12]
Anthony Calabria: "Understanding Lead-Off Detection in ECG". Texas Instruments, Application Report. SBAA196A, May 2012, Revised January 2015. http://www.ti.com/lit/an/sbaa196a/sbaa196a.pdf

What is claimed is:

1. An arrangement comprising:
   an imaging device; and
   a differential voltage measuring system that measures a bioelectric signal including
      an electrode,
      a shunt resistor arranged in series with the electrode in an electric transmission path of the differential voltage measuring system,
      an electrode-status-determining facility for determining electrode status information relating to the electrode for measuring a bioelectric signal, the electrode status information indicating whether the electrode is connected or not connected, and
      a voltage measuring facility switchable parallel to the shunt resistor.

2. The arrangement of claim 1, wherein the imaging device includes a control device, a raw imaging data acquisition device and an image reconstruction facility, and wherein the control device is embodied to control at least one of the raw imaging data acquisition device and the image reconstruction.

3. The arrangement of claim 1, wherein the electrode-status-determining facility is configured to determine whether the electrode is connected or not connected to a patient.

4. The arrangement of claim 1, wherein the electrode is right-leg drive electrode.

* * * * *